United States Patent
Wang et al.

(10) Patent No.: US 11,160,839 B2
(45) Date of Patent: Nov. 2, 2021

(54) PEDIOCOCCUS PENTOSACEUS CCFM1012 AND APPLICATION THEREOF TO PREPARATION OF CAMPYLOBACTER JEJUNI INFECTION ANTAGONISM MEDICINE

(71) Applicant: Jiangnan University, Wuxi (CN)

(72) Inventors: Gang Wang, Wuxi (CN); Wei Chen, Wuxi (CN); Xing Jin, Wuxi (CN); Jianxin Zhao, Wuxi (CN); Hao Zhang, Wuxi (CN)

(73) Assignee: Jiangnan University, Wuxi (CN)

(*) Notice: Subject to any disclaimer, the term of this patent is extended or adjusted under 35 U.S.C. 154(b) by 0 days.

(21) Appl. No.: 17/019,867

(22) Filed: Sep. 14, 2020

(65) Prior Publication Data
US 2021/0069265 A1 Mar. 11, 2021

Related U.S. Application Data

(63) Continuation of application No. PCT/CN2018/079153, filed on Mar. 15, 2018.

(51) Int. Cl.
| A61K 35/744 | (2015.01) |
| A61P 31/04 | (2006.01) |
| A61K 9/00 | (2006.01) |
| A61K 47/02 | (2006.01) |
| A61K 47/36 | (2006.01) |
| A61K 47/38 | (2006.01) |

(52) U.S. Cl.
CPC .......... *A61K 35/744* (2013.01); *A61K 9/0056* (2013.01); *A61K 47/02* (2013.01); *A61K 47/36* (2013.01); *A61K 47/38* (2013.01); *A61P 31/04* (2018.01)

(58) Field of Classification Search
None
See application file for complete search history.

(56) References Cited

FOREIGN PATENT DOCUMENTS

| CN | 101081295 A | 12/2007 |
| CN | 107404913 A | 11/2017 |

*Primary Examiner* — Padmavathi Baskar
(74) *Attorney, Agent, or Firm* — IPRO, PLLC; Na Xu

(57) ABSTRACT

The disclosure discloses *P. pentosaceus* CCFM1012, fermented food thereof and application thereof to preparation of a *C. jejuni* infection antagonism medicine. The *P. pentosaceus* CCFM1012 of the disclosure can remarkably reduce a colonization rate of in-vivo *C. jejuni* of mice infected with *C. jejuni* and transcriptional activity of virulence genes flaA, cadF, cdtB, cdtC and dnaJ of the *C. jejuni*, can effectively relieve physiological damage caused by infection of the *C. jejuni*, can also be used for preparing dairy products, bean products and fruit and vegetable fruits for preventing infection of the *C. jejuni* and an additive that can be added to a poultry and livestock feed for reducing infection and carrying of the *C. jejuni* in poultry and livestock, and has quite broad application prospects.

9 Claims, 5 Drawing Sheets
Specification includes a Sequence Listing.

PEDIOCOCCUS PENTOSACEUS CCFM1012 AND APPLICATION THEREOF TO PREPARATION OF CAMPYLOBACTER JEJUNI INFECTION ANTAGONISM MEDICINE

TECHNICAL FIELD

The disclosure relates to *Pediococcus pentosaceus* CCFM1012 and application thereof to preparation of a *Campylobacter jejuni* infection antagonism medicine, and belongs to the technical field of microorganisms.

BACKGROUND

*Campylobacter jejuni* is gram-negative bacteria. The *C. jejuni* is widely distributed in nature, can spread through animals, foods, water, milk and the like, and can colonize in intestines of various kinds of wild animals, poultry and livestock. Human beings may be infected by making contact with poultry and livestock, eating undercooked or contaminated chicken and beef and drinking milk that is not thoroughly sterilized and drinking contaminated water. In recent years, the infection rate of the *C. jejuni* generally maintains an upward trend all over the world. In some developed countries, the number of diarrhea cases caused by infection of the *C. jejuni* even exceeds that of *Salmonella* and *Shigella*, which makes the *C. jejuni* the most common diarrhea pathogenic bacteria. In developing countries, the *C. jejuni* is the most common pathogenic bacteria that cause infantile infectious diarrhea. People are most likely to suffer enterogastritis, diarrhea, fever and abdominal colic after being infected with the *C. jejuni*, and immunocompromised people may further suffer from complications, such as cholecystitis, peritonitis, meningitis, sepsis and osteomyelitis. The most severe complication caused by the *C. jejuni* is Guillian-Barré Syndrome (GBS), which may cause axonal damage and irreversible nerve damage, even death from respiratory muscle paralysis.

Antibiotics are a common method for clinical treatment of infection of the *C. jejuni* at present, but the use of the antibiotics may cause the tolerance of the *C. jejuni* and enteric bacteria to the antibiotics, and the excessive use of the antibiotics even may cause residual in-vivo antibiotics. An edible strain with an antagonism effect on the *C. jejuni* is screened from nature, which is beneficial for enriching measures of relieving infection of the *C. jejuni*, and improving efficiency of treating diseases caused by infection of the *C. jejuni*.

SUMMARY

The disclosure provides *P. pentosaceus* CCFM1012 which is deposited in GuangDong Microbial Culture Collection Center on Feb. 11, 2018. Deposit address: Guangdong Institute of Microbiology, 5th Floor, No. 59 Building, No. 100 Yard, Xianlie Middle Road, Guangzhou. Deposit number: GDMCC No. 60331.

The disclosure further provides a composition containing the *P. pentosaceus* CCFM1012.

In one embodiment, the composition is a feed additive.

In one embodiment, the feed additive is a feed additive finished product containing the *P. pentosaceus* CCFM1012 with a viable count of larger than or equal to $1\times10^{10}$ CFU/g, and is obtained by mixing bacterial cells of the *P. pentosaceus* CCFM101 with a solution of sodium carboxymethylcellulose accounting for 40% of a wet weight of the bacteria, microcrystalline cellulose 8 times a wet weight mass of the bacteria, sodium alginate 10 times a mass of the bacteria, calcium chloride 10 times a mass of the bacteria and water 20 times a mass of the bacteria, then performing wet granulating and performing cyclone drying at 37° C.

In one embodiment, the composition is a fermented food prepared by fermenting the *P. pentosaceus* CCFM1012. The fermented food includes dairy products, bean products and fruit and vegetable products. The dairy products include milk, sour cream and cheese. The fruit and vegetable products include cucumber products, carrot products, beet products, celery products and cabbage products.

In one embodiment, the composition is a microbial preparation.

In one embodiment, the microbial preparation is a cell culture fluid of the *P. pentosaceus* CCFM1012.

In one embodiment, the cell culture fluid is a cell culture fluid obtained by culturing the *P. pentosaceus* CCFM1012 in an MRS medium.

In one embodiment, the *P. pentosaceus* CCFM1012 has a cell concentration of larger than or equal to $1\times10^{7}$ CFU/mL.

In one embodiment, the microbial preparation is a freeze-dried preparation containing viable cells of the *P. pentosaceus* CCFM1012, and is prepared by fermenting the *P. pentosaceus* CCFM1012 in an MRS medium, collecting bacterial cells, mixing the bacterial cells with a cytoprotective agent and then performing freeze-drying treatment.

The disclosure further provides application of the *P. pentosaceus* CCFM1012 to preparation of in-vivo colonization probiotics.

The disclosure further provides application of the *P. pentosaceus* CCFM1012 to preparation of a *C. jejuni* infection antagonism medicine.

In one embodiment, the application has at least one of the following functions:

(1) restraining growth of *C. jejuni*;
(2) reducing an in-vivo colonization quantity of the *C. jejuni*;
(3) lowering expression levels of virulence genes flaA, cadF, cdtB, cdtC and dnaJ of the *C. jejuni*; and
(4) relieving physiological damage caused by infection of the *C. jejuni*.

In one embodiment, the fermented food can restrain the growth of the *C. jejuni*, reduce the in-vivo colonization quantity of the *C. jejuni*, lower the expression levels of the virulence genes flaA, cadF, cdtB, cdtC and dnaJ of the *C. jejuni*, and relieve the physiological damage caused by the infection of the *C. jejuni*.

In one embodiment, the medicine is a liquid, a powder or a granule containing the *P. pentosaceus* CCFM1012.

The disclosure further provides application of the *P. pentosaceus* CCFM1012 to preparation of the *C. jejuni* infection antagonism feed additive. The feed additive can reduce infection and carrying of the *C. jejuni* in poultry and livestock.

The disclosure further provides application of the *P. pentosaceus* CCFM1012 or the fermented food of the *P. pentosaceus* CCFM1012 to preparation of *C. jejuni* infection antagonism functional food.

The disclosure has the beneficial effects: the *P. pentosaceus* CCFM1012 has a good gastric acid resistant property and a good bile salt resistant property, has a quite strong restraining effect on growth of *C. jejuni*, has an inhibition zone of 15.65±0.47 (mm) in an Oxford cup experiment, and meanwhile has a quite good adhesive capacity to intestinal epithelial cells. An adhesion index can reach 15.7±2.1. The life of *elegans* infected with the *C. jejuni* can be prolonged by just a single bacterium. The colonization quantity of in-vivo *C. jejuni* of mice infected with the *C. jejuni* and transcriptional activity of the virulence genes flaA, cadF, cdtB, cdtC and dnaJ of the *C. jejuni* can be remarkably reduced, and the physiological damage caused by the infection of the *C. jejuni* can be effectively relieved.

The *P. pentosaceus* CCFM1012 of the disclosure can be used for preparing the dairy products, bean products and fruit and vegetable products for preventing the infection of the *C. jejuni*, can also be used for preparing an additive that can be added to a poultry and livestock feed for reducing the infection and carrying of the *C. jejuni* in poultry and livestock, and has quite broad application prospects.

Deposit of Biomaterial

The *P. pentosaceus* CCFM1012 is deposited in GuangDong Microbial Culture Collection Center on Feb. 11, 2018. Deposit address: Guangdong Institute of Microbiology, 5th Floor, No. 59 Building, No. 100 Yard, Xianlie Middle Road, Guangzhou. Deposit number: GDMCC No. 60331.

DETAILED DESCRIPTION

Figure 1:
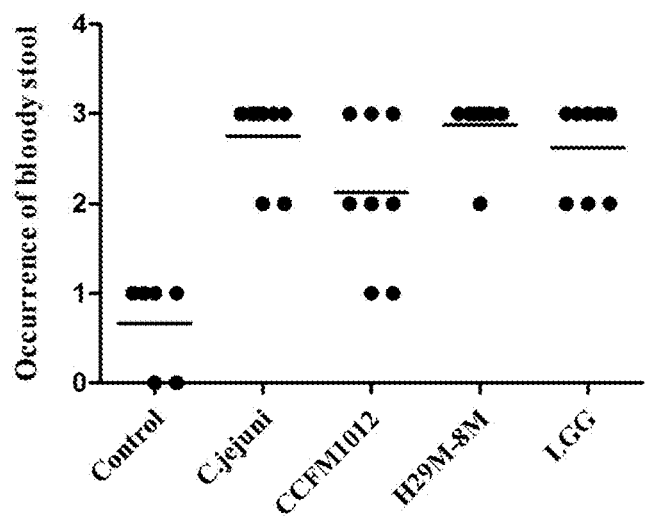
FIG. 1 is a schematic diagram that shows influences of a strain of the disclosure on stool occult blood of mice infected with *C. jejuni*.

The *P. pentosaceus* CCFM1012 of the disclosure is deposited in GuangDong Microbial Culture Collection Center on Feb. 11, 2018. Deposit address: Guangdong Institute of Microbiology, 5th Floor, No. 59 Building, No. 100 Yard, Xianlie Middle Road, Guangzhou. Deposit number: GDMCC No. 60331.

The *P. pentosaceus* CCFM1012 has the Following Biological Properties:

(1) bacterial characteristics: the bacteria are gram-positive, has globoid cells, has a diameter of 0.8-1.0 µm, and has no flagella or spores;

(2) colony characteristics: the colony has a milk white color and neat edges, is globoid, protruding, opaque and has a wet and smooth surface;

(3) growth properties: the lowest growth temperature of the strain is 15° C. and the highest growth temperature is 45° C., the best growth temperature is 35-37° C., an optimum growth pH is 6.5, and the strain enters a stationary phase after being cultured for 18 h;

(4) a good gastric acid resistant property and a good bile salt resistant property are obtained;

(5) the growth of *C. jejuni* in vitro can be remarkably restrained;

(6) the adhesive capacity to intestinal epithelial cells is good;

(7) the *P. pentosaceus* can remarkably prolong the life of elegans infected with *C. jejuni* in a *Caenorhabditis elegans* infection model;

(8) the *P. pentosaceus* can effectively reduce a colonization quantity of in-vivo *C. jejuni* of mice infected with *C. jejuni*; and (9) the *P. pentosaceus* can remarkably restrain transcriptional activity of virulence genes flaA, cadF, cdtB, cdtC and dnaJ, and the like of in-vivo *C. jejuni* of mice infected with *C. jejuni*.

Extraction Method of the *P. pentosaceus* CCFM1012

(I) Separating and screening of lactic acid bacteria:

(1) a plurality stool samples of healthy domestic chickens are collected, and the samples are enriched in a culture medium containing sorbitol GM17 for 12 h at 35° C.;

(2) gradient dilution is performed on the enriched samples, and the samples are coated on a GM17 solid plate with 0.02% of added bromcresol purple and cultured for 24-48 h;

(3) a single colony which has an obvious discoloration circle and satisfies a basic morphology of lactic acid bacteria is selected for plate streak purification, and lactic acid bacteria are screened and separated out; and (4) the single colony is cultured in a liquid GM17 culture solution for 24 h for gram staining, and gram-positive bacteria are selected for subsequent testing.

(II) Primary identification of lactic acid bacteria: a calcium dissolving zone measuring method (1) the lactic acid bacteria screened out in step (I) are cultured in a liquid sorbitol GM17 culture solution for 24 h, and then 1 mL of culture is taken and centrifuged for 2 min at 8000 rpm;

(2) washing is performed twice with a 0.05 M $KH_2PO_4$ solution;

(3) obtained bacterial sludge is resuspended, streaked into a sorbitol GM17-0.75% $CaCO_3$ solid culture medium and cultured for 24 h; and (4) a colony which has an obvious calcium dissolving zone and is convex circular, dense and white and free of mycelia is selected, and coccus is primarily recognized when bacteria are globoid as observed with a microscope after gram staining.

(III) Molecular biological identification of lactic acid bacteria:

(1) a genome of single bacteria is extracted:

A. the lactic acid bacteria screened out in step (II) are cultured overnight, 1 mL of a bacterial suspension cultured overnight is put into a 1.5 mL centrifuge tube and centrifuged for 2 min at 10000 rpm, and bacteria are obtained after supernate is discarded;

B. the bacteria are purged with 1 mL of sterile water and then centrifuged for 2 min at 10000 rpm, and bacteria are obtained after supernate is discarded;

C. 200 µL of SDS lysate is added for water bath for 30 min at 80° C.;

D. 200 µL of a phenol-chloroform solution is added to bacteria lysate, after bottom-up even mixing, centrifuging is performed for 5-10 min at 12000 rpm, and 200 µL of supernate is taken, wherein the phenol-chloroform solution has compositions of Tris-saturated phenol, chloroform and isoamyl alcohol according to a volume ratio of 25:24:1;

E. 400 µL of ice alcohol or ice isopropyl alcohol is added to 200 µL of supernate to stand for 1 h at −20° C. and is then centrifuged for 5-10 min at 12000 rpm, and supernate is taken;

F. 500 μL of 70% (volume percentage) ice alcohol is added for resuspending precipitates and centrifuged for 1-3 min at 12000 rpm, and supernate is discarded;

G. drying is performed with an oven at 60° C., or air-drying is performed; and

H. 50 μL of ddH$_2$O is added for redissolving precipitates for PCR; and (2) 16S rDNA PCR is performed A. bacteria 16S rDNA 50 μL PCR system:

10×Taq buffer, 5 μL; dNTP, 5 μL; 27 F, 0.5 μL; 1492 R, 0.5 μL; Taq enzyme, 0.5 μL; template, 0.5 μL; ddH$_2$O, 38 μL.

B. PCR conditions:

95° C. 5 min; 95° C. 10 s; 55° C. 30 s; 72° C. 30 s; step 2-4 30×; 72° C. 5 min; 12° C. 2 min;

(3) 1% agarose gel is prepared, then a PCR product is mixed with a 10000× loading buffer, a loading quantity of sample is 5 μL, running is performed for 30 min at 120 V, and then gel imaging is performed; and (4) a PCR product of 16S rDNA is subjected to sequencing analysis, an obtained sequence result is subjected to searching and similarity comparing in a GeneBank by using BLAST, and a new-found strain identified as *P. pentosaceus* in a sequencing result is selected and preserved at −80° C. for use.

Example 1: Tolerance of *P. pentosaceus* CCFM1012 to Stimulated Gastrointestinal Juice The cryopreserved *P. pentosaceus* CCFM1012 is streaked and inoculated into an MRS solid culture medium and aerobically cultured for 48 h at a temperature of 37° C. and then subcultured 2-3 times in an MRS culture solution, a *P. pentosaceus* CCFM1012 culture solution is taken and centrifuged for 5 min at 8000 r/min to collect bacteria, the bacteria are resuspended in (1:1) pH-2.5 artificial stimulated gastric juice (containing 1% pepsase and a pH-2.5 MRS medium) and mixed and then anaerobically cultured at 37° C., sampling is performed at start time (0 h), 1 h, 2 h and 3 h respectively, pouring culturing is performed through an MRS agar culture medium for plate colony counting, a viable count is measured, and its survival rate is calculated. The survival rate is a ratio of a viable count in the culture solution to a viable count at 0 h, which is represented by %.

The *P. pentosaceus* CCFM1012 culture solution is taken and centrifuged for 5 min at 8000 r/min to collect bacteria, the bacteria are resuspended in (1:1) artificial stimulated intestinal juice (containing 0.3% bile salt, 1% trypsin and a pH-8.0 MRS medium) to be aerobically cultured at 37° C., sampling is performed at 0 h, 1 h, 2 h, 3 h and 4 h respectively, pouring culturing is performed through an MRS agar culture medium for plate colony counting, a viable count is measured, and its survival rate is calculated. The survival rate is a ratio of a viable count in the culture solution to a viable count at 0 h, which is represented by %. Experimental results are shown in Table 1 and Table 2, and it can be seen that the *P. pentosaceus* CCFM1012 has good tolerance to both the artificial stimulated gastric juice and the artificial stimulated intestinal juice.

TABLE 1

Tolerance of *P. pentosaceus* CCFM1012 in artificial stimulated gastric juice

| | Artificial stimulated gastric juice | | |
|---|---|---|---|
| Processing time (h) | 1 | 2 | 3 |
| Survival rate (%) | 95.45 ± 2.36 | 88.37 ± 4.26 | 82.59 ± 3.77 |

TABLE 2

Tolerance of *P. pentosaceus* CCFM1012 in artificial stimulated intestinal juice

| Processing | Artificial stimulated intestinal juice | | | |
|---|---|---|---|---|
| time (h) | 1 | 2 | 3 | 4 |
| Survival rate (%) | 81.41 ± 3.57 | 74.99 ± 6.28 | 69.71 ± 5.03 | 61.88 ± 5.29 |

Example 2: *P. pentosaceus* CCFM1012 In-Vitro Restrains Growth of *C. jejuni*

Strains of *P. pentosaceus* CCFM1012, *P. pentosaceus* H29M-8M and *Lactobacillus rhamnosus* LGG are taken out of a refrigerator at −80° C. and streaked into an MRS plate and cultured for 48 h at 37° C., a single colony is selected and put into an MRS liquid tube, and cultured for 18 h at 37° C., then 2% (volume) of the single colony is inoculated into a new MRS liquid culture medium and cultured for 18 h at 37° C., one another generation is cultured in the same way, then a lactic acid bacteria suspension is centrifuged for 8 min at 8000 r/min and 4° C., supernate is sucked, a 0.22 μm water-based filter membrane is used for filtering sterilization to obtain lactic acid bacteria fermented supernate, and a fermentation broth is regulated to a pH of 6.5 with 1 mol/L NaOH.

A strain of *C. jejuni* NCTC11168 (purchased from American Type Culture Collection ATCC) is cultured in two culture mediums (namely *Brucella* agar from Qingdao Haibo Biotechnology Co., Ltd. and brain heart infusion broth medium from Oxoid Company) at a temperature of 37° C. under a three-gas environment with 5% $O_2$, 10% $CO_2$ and 85% $N_2$, subcultured for two generations in the same way, centrifuged for 6 min at 2800 r/min, washed with a phosphate buffer solution (PBS, pH=7.2), and then resuspended in the PBS to reach a bacterial concentration of $10^8$ CFU/mL.

A *C. jejuni* bacteria suspension (250 μL, $10^8$ CFU/mL) is sucked and evenly coated into a Columbia blood agar plate, an Oxford cup is placed after the bacteria solution is naturally dried, 100 μL of lactic acid bacteria fermented supernate (pH=6.5) is added into the Oxford cup and dispersed for 2 h at 4° C., then the Oxford cup is put into a three-gas incubator and cultured for 48 h at 37° C., and then a diameter of an inhibition zone is measured. With an added sterilized MRS with a pH of 6.5 as a negative control and a 0.30 mg/mL norfloxacin broad-spectrum antibiotic as a positive control, a diameter (mm) of the inhibition zone is detected.

TABLE 3

Measurement results of diameter of inhibition zone

| Strain | Diameter (mm) of inhibition zone |
| --- | --- |
| CCFM1012 | 15.65 ± 0.47 |
| H29M-8M | 7.56 ± 0.13 |
| LGG | 10.39 ± 0.78 |
| MRS (pH = 6.5) | 7.37 ± 0.51 |
| 0.30 mg/mL norfloxacin | 19.72 ± 0.83 |

An antibacterial effect is shown in Table 3, and the results show that the *P. pentosaceus* CCFM1012 fermented supernate remarkably restrains growth of *C. jejuni*, the diameter of its inhibition zone can reach 15.65±0.47 (mm), and its effects are remarkably better than those of control groups *P. pentosaceus* H29M-8M and *L. rhamnosus* LGG.

Example 3: Adhesive Capacity of *P. pentosaceus* CCFM1012 to Intestinal Epithelial Cells HT-29

An RPMI1640 culture solution (Gibco Company) with 10% fetal calf serum and 1% mycillin added is used for culturing intestinal epithelial cell strain HT-29 cells (purchased from Cell Bank of China Center for Type Culture Collection). The HT-29 cells are cultured at 37° C. in a cell incubator containing 5% $CO_2$, the culture solution is replaced once every 48 h during culturing, and culturing is continuous.

The HT-29 cells growing and fusing to 70-80% are dissociated, a concentration is regulated to $2\times10^5$ cells/mL, a sterile cover glass is placed in a 6-pore cell culture plate, 2 mL of a cell culture suspension is added into each pore, culturing is performed at 37° C. in the incubator containing 5% $CO_2$, when the cells grow to a monolayer, the cells are washed three times with a PBS, 1 mL of a serum-free and antibiotic-free RPMI-1640 cell culture bacterial suspension containing $2\times10^8$ CFU/mL lactic acid bacteria is added into each pore, an RPMI-1640 cell culture solution (containing no serum or antibiotics) is added to 2 mL, and incubation is performed for 2 h. After incubation ends, washing is performed three times with a PBS to remove non-adhesive lactic acid bacteria, fixation is performed for 20 min with methyl alcohol, gram staining is performed after three times of washing with the PBS, and microscopic examination is carried out under a 100× oil immersion lens. A count of bacteria adhering to every 100 cells is calculated as an adhesion index by randomly selecting 20 views. Adhesion experimental results are listed in Table 4.

TABLE 4

Adhesion conditions of lactic acid bacteria on surfaces of HT-29 cells

| Strain name | Adhesion index |
| --- | --- |
| CCFM1012 | 15.7 ± 2.1 |
| H29M-8M | 1.2 ± 0.2 |
| LGG | 13.2 ± 1.9 |

It can be seen from the results of Table 4 that the *P. pentosaceus* CCFM1012 has a high adhesive capacity to the intestinal epithelial cells HT-29 and has an adhesion index of 15.7±2.1, its adhesive capacity is better than that of control groups *P. pentosaceus* H29M-8M and *L. rhamnosus* LGG, and the *P. pentosaceus* CCFM1012 with high adhesive capacity can effectively prevent pathogenic microorganisms from making contact with and adhering to intestinal mucosal cells after colonizing in intestines, thereby preventing intestinal diseases caused by pathogenic entero bacteria.

Example 4: Influences of *P. pentosaceus* CCFM1012 on Life of *Caenorhabditis Elegans* Infected with *C. jejuni*

Preparation of *E. coli* OP50: *E. coli* OP50 is inoculated into a liquid culture medium for shaking culturing, and when OD600 is 1.0-1.2, after even mixing by shaking, a bacteria solution is sucked and dropwise added onto a *Caenorhabditis elegans* growth NGM plate and evenly coated for culturing and storing for use.

Recovery and synchronization of *Caenorhabditis elegans*: an *elegans* cryopreservation tube is frozen and thawed, and centrifuged, supernate is discarded, and the *elegans* is poured into the NGM plate with growing *E. coli* OP50 for recovery; after the *elegans* grows into an adult, sterile water is sucked by a liquid transfer gun to flush the plate repeatedly, liquid containing *elegans* is transferred into a centrifuge tube, a sterile water suspension containing *elegans* is sucked and added into a new centrifuge tube, and a sodium hydroxide solution and a sodium hypochlorite solution are added and sufficiently mixed evenly; the centrifuge tube is observed under a microscope after every 2-3 min of shaking until no large *elegans* fragments can be seen; centrifuging and washing with sterile water are performed; and an S culture medium solution is used for resuspending to culture eggs contained therein and centrifuged to collect L1-phase *elegans*, and the *elegans* is transferred into an NGM culture plate with growing *E. coli* OP50 and cultured for 72 h at 20° C. to obtain L4-phase *elegans*.

TABLE 5

Statistical analysis of life of elegans infected with *C. jejuni* after intervention by lactic acid bacteria

| Group | Survival rate[a] (%) | DT50[b] (day) | P value |
| --- | --- | --- | --- |
| *E. coli* + *C. jejuni* | 20.16 | 6.83 | |
| *E. coli* | 55.78 | 14.90 | <0.01 |
| CCFM1012 + *C. jejuni* | 45.81 | 14.46 | <0.01 |
| H29M-8M + *C. jejuni* | 22.17 | 7.81 | 0.55 |
| LGG + *C. jejuni* | 21.05 | 7.65 | 0.57 | a: a survival rate of *elegans* on the 13th day is calculated with a Kaplan-Meier survival model; and b: DT50, time required for 50% of *elegans* to die.

In a processing mode of the *elegans* in Table 5, the L4-phase *elegans* is picked by a sterile *elegans* picker and transferred into improved NGM plates, about 80-100 *elegans* are contained in each plate, 200 µL of *E. coli* OP50 and lactic acid bacteria bacterial suspension with a final concentration of $10^8$ CFU/mL is added to a control group (*E. coli*+*C. jejuni*) and intervention groups (CCFM1012+*C. jejuni*, H29M-8M+*C. jejuni* and LGG+*C. jejuni*) respectively, hereafter viable *elegans* are transferred into new improved NGM plates every day, corresponding bacterial suspensions are added to different groups correspondingly, three days later, the intervention groups stop being fed with lactic acid bacteria, 200 µL of a $10^8$ CFU/mL *C. jejuni* bacterial suspension is added to the control group and the intervention groups respectively, hereafter, viable *elegans* are transferred into new NGM plates every day, 200 µL of a $10^8$ CFU/mL *C. jejuni* bacterial suspension is added to each group, *elegans* in a blank group (*E. coli*) are transferred into a new NGM plate, *E. coli* OP50 with a final concentration of $10^8$ CFU/mL is added, and the number of dead *elegans* in each group is recorded. It can be seen from the results in the figure that the *P. pentosaceus* CCFM1012 can remarkably prolong the life of *elegans* infected with *C. jejuni*, a survival rate of *elegans* can still reach 45.81% on the 13th day in the CCFM1012+*C. jejuni* group, furthermore, the number of days for 50% of *elegans* to die is prolonged to 14.46, and the prolonging effect is obviously better than that of *P. pentosaceus* H29M-8M and *L. rhamnosus* LGG.

Example 5: Antagonism Effect of *P. pentosaceus* CCFM1012 on In-Vivo *C. jejuni* of Mice Infected with *C. jejuni*

The example adopts C57BL/6 mice diversely infected with *Toxoplasma gondii* and *C. jejuni* as laboratory mice, and *C. jejuni* can largely colonize in mice infected with *Toxoplasma gondii*.

Preparation of Mice Gavage Agent

*C. jejuni* gavage agent: activated $2^{nd}$-generation *C. jejuni* is taken and cultured for 24 h at 37° C. under a three-gas condition and centrifuged for 6 min at 4° C. and 2800 r/min to collect bacteria, supernate is discarded, and the bacteria are resuspended with a sterile phosphate buffer solution, so that a concentration of *C. jejuni* reaches $3 \times 10^9$ CFU/mL.

Lactic acid bacteria gavage agent: activated 2nd-generation lactic acid bacteria is taken and cultured for 24 h at 37° C. under a three-gas condition (5% $O_2$, 10% $CO_2$ and 85% $N_2$) and centrifuged for 3 min at 4° C. and 8000 r/min to collect bacteria, supernate is discarded, and the bacteria are resuspended with a sterile phosphate buffer solution, so that a concentration of lactic acid bacteria reaches $5 \times 10^9$ CFU/mL.

*Toxoplasma gondii* gavage agent: cerebrum tissue is taken after mice chronically infected with *Toxoplasma gondii* Me49 are killed, a sterile phosphate buffer solution is added, and sufficient grinding is performed. 10 µL of cerebrum homogenate is dropwise added onto a glass slide, counting is performed under a light microscope, and this step is repeated 3 times. A concentration of the cerebrum homogenate is regulated according to a counting result, and each mouse is fed by gavage of 200 µL of cerebrum homogenate, so that a dosage of the *Toxoplasma gondii* gavage agent reaches 20 cysts per mouse.

Grouping and Processing of Mice:

Each experimental group has 8 mice, 4 mice are grouped into one cage, and a gavage agent dosage of all the mice is 300 µL per mouse. On the 1st day of an animal experiment, except the mice in the control group, other mice are fed by gavage of *Toxoplasma gondii* cyst pathogens; the mice are normally fed on the 2nd day, the 3rd day and the 4th day so that the pathogens start to damage immune system of the mice; on the 5th day and the 6th day, the mice are fed by gavage of lactic acid bacteria and *C. jejuni* sequentially, and the internal between two times of gavage is at least 1 h, so that the gavage agents are prevented from influencing each another; the mice show symptoms of infection of *C. jejuni* on the 7th day, the 8th day, the 9th day and the 10th day; the mice are killed on the 11th day, which means the animal experiment comes to an end. A detailed grouping and processing method is shown in Table 6.

TABLE 6

Grouping and processing method of laboratory mice

| Group | Processing mode | | | | |
|---|---|---|---|---|---|
| | 1st day | 2-4th day | 5-6th day | 7-10th day | 11th day |
| Control | PBS | Normally fed | PBS + PBS | Normally fed | Killed |
| C.j | T.g | Normally fed | PBS + C.j | Normally fed | Killed |
| CCFM1012 | T.g | Normally fed | CCFM1012 + C.j | Normally fed | Killed |
| H29M-8M | T.g | Normally fed | H29M-8M + C.j | Normally fed | Killed |
| LGG | T.g | Normally fed | LGG + C.j | Normally fed | Killed |

Detection of stool occult blood of mice: one fresh collected mouse stool is taken for stool occult blood detection with a stool and urine occult blood kit. An experimental method includes the following steps: the stool is evenly coated on white filter paper, 3 drops of o-tolidine solution are dropwise added, then 2 drops of hydrogen peroxide are dropwise added, and developing results are observed as follows:

when a blue-green color is not developed 3 min later, it ends up with a negative result and a score of 0;

when a blue color is developed within 30-60 s, it ends up with a weakly positive result and a score of 1;

when a blue-green color is developed instantly, it ends up with a positive result and a score of 2; and when a dark blue color is developed instantly, it ends up with a strongly positive result and a score of 3.

Detection of viable count of *C. jejuni* in mouse stool: fresh mouse stool is taken and precisely weighed and then soaked in a sterile saline solution for 30 min so as to be softened, a stool suspension is sufficiently mixed evenly and subjected to gradient dilution, 100 pi of diluent with a proper gradient is selected and evenly coated on the Columbia blood plate with added *campylobacter* selective antibiotics and the Columbia blood plate is put into a three-gas incubator and cultured for 48 h at 37° C., and *C. jejuni* colonies growing on the plate are counted.

Mouse colon paraffin section making, HE dyeing and pathological scoring: colon tissue soaked in paraformaldehyde with a mass percentage of 4% is taken out for paraffin section making and HE dyeing.

Paraffin section making steps are as follows: colon tissue is sequentially put into ethanol with a volume fraction of 70%, 80%, 90%, 95% and 100% for 20 min each for dewatering, the dewatered colon tissue is put into an 1:1 solution of ethanol and xylene for 5 min, then colon is soaked in xylene twice for 15 min each, and the colon is waxed and then sectioned with a thickness of about 5 µm.

HE dyeing steps are as follows: dewaxing is performed twice with xylene for 5 min each, then sections are soaked in ethanol with a volume fraction of 100%, 95%, 80% and 70% for 5 min each, and the sections are flushed with flowing water for 5 min, dyed with hematoxylin for 5 min and washed twice with ultrapure water. The sections are put into a hydrochloric acid ethanol (hydrochloric acid with a volume fraction of 0.5% is added to ethanol with a volume fraction of 70%) for color separation for 10 s, flushed with flowing water for 10 min, and then sequentially put into ethanol with a volume fraction of 70%, 80% and 95% for 5 min each. The sections are dyed for 5 min with eosin ethanol (eosin with a volume fraction of 0.5% is added to ethanol with a volume fraction of 95%), then sequentially put into ethanol with a volume fraction of 95% and 100% for 5 min each, transparentized twice with xylene and finally sealed with neutral balsam.

The sections are read through a blind method under a microscope and pathological scoring is performed, and scoring standards are shown in Table below:

TABLE 7

Colon tissue pathological scoring standards

| Type | Visible colon features under microscope | Score |
|---|---|---|
| Intestinal epithelial cell | Normal morphology | 0 |
| | Injured goblet cell | 1 |
| | Goblet cell disappearance | 2 |
| | Injured crypt gland | 3 |
| | Lost crypt gland | 4 |
| Inflammatory cell infiltration | No inflammatory cell infiltration | 0 |
| | Inflammatory cell infiltration around crypts | 1 |
| | Inflammatory cell penetration to muscularis mucosa | 2 |
| | Inflammatory cell penetration to muscularis mucosa, wide range, mucous layer edema | 3 |
| | Inflammatory cell penetration to submucosa | 4 |

Mouse stool is collected, its occult blood conditions are evaluated through a stool occult blood kit, and the results are shown in FIG. 1. The results show that the stool occult blood conditions of mice diversely infected with *Toxoplasma gondii* and *C. jejuni* are severe, after intervention by the *P. pentosaceus* CCFM1012, the stool occult blood symptoms of the mice are remarkably relieved, stool occult blood scores of the mice are lowered to 2.15, and compared with *P. pentosaceus* H29M-8M and *L. rhamnosus* LGG, the *P. pentosaceus* CCFM1012 has a more active relieving effect.

Figure 2:
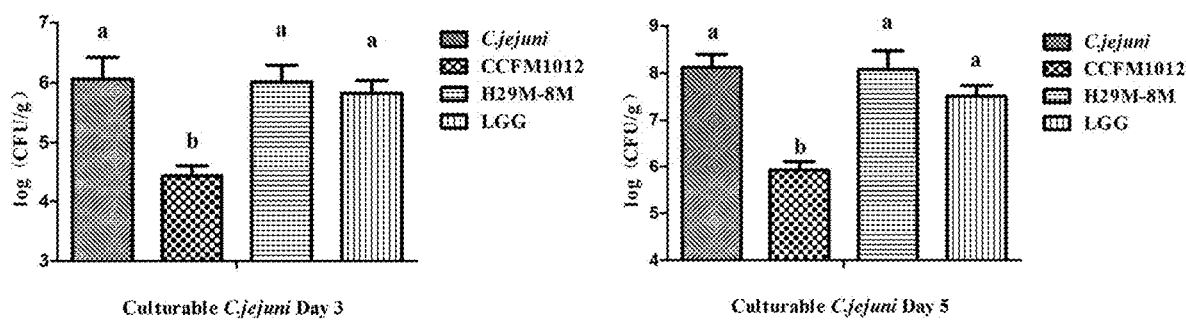
FIG. 2 is a schematic diagram that shows variations of a colonization quantity of in-vivo *C. jejuni* of mice infected with *C. jejuni* three days and five days after intervention by the strain of the disclosure.

As shown in FIG. 2, *P. pentosaceus* CCFM1012 can effectively reduce a colonization quantity of in-vivo *C. jejuni* of mice. In the C.j group, detectable quantities of *C. jejuni* in the in-vivo stool on the third day and the fifth day can reach $10^6$ and $10^8$ CFU/g feces, and as time goes by, the colonization quantity gradually rises. In the intervention group of *P. pentosaceus* CCFM1012, the colonization quantity of *C. jejuni* on the third day can be reduced to $10^4$-$10^5$ CFU/g feces, which drops by about 1.5 orders of magnitude compared with that of the control group. The colonization quantity of in-vivo *C. jejuni* of mice is accordingly improved on the fifth day since the mice are more and more severely infected with *Toxoplasma gondii*, but the *Pediococcus pentosaceus* CCFM1012 still has a good eradication ability after intervention, and the colonization quantity of *C. jejuni* can be reduced to $10^6$ CFU/g feces, which drops by about two orders of magnitude. The eradication rate of the *P. pentosaceus* CCFM1012 for in-vivo *C. jejuni* of mice is far higher than that of processing groups of *P. pentosaceus* H29M-8M and *L. rhamnosus* LGG.

Figure 3A:
FIG. 3A-3E is a schematic diagram that shows pathological sections of colon tissue of mice infected with *C. jejuni* after intervention by the strain of the disclosure.
Figure 3B:
Figure 3C:
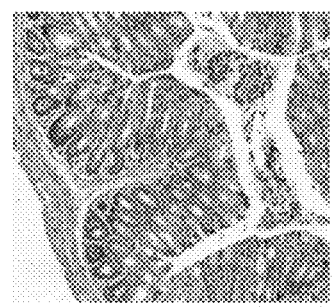
Figure 3D:
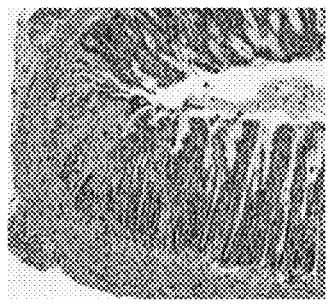
Figure 3E:
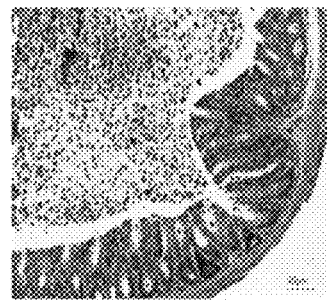
Figure 4:
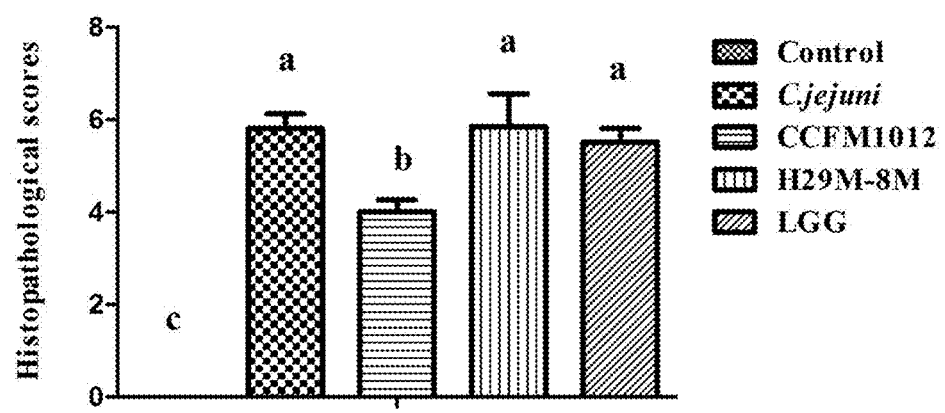
FIG. 4 is a schematic diagram that shows pathological scores of colon tissue of mice infected with *C. jejuni* after intervention by the strain of the disclosure.

HE dyeing results are observed under a microscope and are shown in FIG. 3A-3E. In the figure, FIG. 3A represents the control group, FIG. 3B represents the C.j group, FIG. 3C represents the CCFM1012 group, FIG. 3D represents the H29M-8M group, and FIG. 3E represents the LGG group. It can be seen from the results that intestinal epithelium and intestinal wall of mice in the control group are complete in structure, normal in cellular morphology and free of adverse changes. The mice diversely infected with *Toxoplasma gondii* and *C. jejuni* suffer from severe colon lesions with typical features of goblet cell disappearance, obvious inflammatory cell infiltration, injured crypt, injured mucosal, etc. In combination with pathological scoring analysis (FIG. 4), the score of the *P. pentosaceus* CCFM1012 group lowers to 4, which greatly relieves colon lesions of mice. The above results show that the *P. pentosaceus* CCFM1012 can relive injuries caused by *C. jejuni* to colons of mice after having an antagonism effect on *C. jejuni*.

Example 6: Influences of *P. pentosaceus* CCFM1012 on Transcriptional Levels of Virulence Genes flaA, cadF, cdtB, cdtC and dnaJ of In-Vivo *C. jejuni* of Mice Infected with *C. jejuni*

An establishing and processing mode of a *C. jejuni* infection mouse model is shown in Example 5.

Designing and synthesizing of q RT-PCR primers of virulence genes flaA, cadF, cdtB, cdtC and dnaJ of *C. jejuni* are shown in Table 8.

TABLE 8 q PCR primers of virulence genes flaA, cadF, cdtB, cdtC and dnaJ of C.jejuni and reference genes

| Target gene | Primer sequence (5'-3') | Primer sequence | Product size |
|---|---|---|---|
| rpoD | F:AGACTCTCCTGTTCGTATGTAT | SEQ ID NO. 1 | 136 bp |
| | R:ATGATAATATCTTCGCCAAGTT | SEQ ID NO. 2 | |
| flaA | F:GCTATGGCTGTGATGGATA | SEQ ID NO. 3 | 119 bp |
| | R:TGAGTTACGGTGATGTTGT | SEQ ID NO. 4 | |
| cadF | F:ACTATTCTTGAAGGACATACA | SEQ ID NO. 5 | 154 bp |
| | R:CGAGGATTATCTTGACCATA | SEQ ID NO. 6 | |
| cdtB | F:ATTGATGAATATGAGTGGAAT | SEQ ID NO. 7 | 155 bp |
| | R:TGTAGTAGGTGGAGGTAA | SEQ ID NO. 8 | |
| cdtC | F:TCAGCTGTGCAAATTCGTTC | SEQ ID NO. 9 | 121 bp |
| | R:AAATAGGATCTAGGGTGCAAGG | SEQ ID NO. 10 | |
| dnaJ | F:AGTGTCGAGCTTAATATCCC | SEQ ID NO. 11 | 117 bp |
| | R:GGCGATGATCTTAACATACA | SEQ ID NO. 12 | |

Total RNA extraction and cDNA synthesis of colon tissue and *C. jejuni*:

0.2 g of fresh colon tissue taken out after dissection of mice is repeatedly ground in a mortar (high-temperature enzyme deactivation for 4 h at 180° C.) with added liquid nitrogen, 1 mL of a Trizol agent is then added into the mortar, grinding continues, after being basically clarified, liquid is collected into a 1.5 mL non-enzyme centrifuge tube to stand for 15 min at a room temperature, 200 μL of a trichloromethane solution is added into the centrifuge tube and slightly shaken for 15 s, stands for 10 min at a room temperature and is then centrifuged for 15 min at 4° C. and 12000 r/min, 600 μL of an upper-layer colorless water phase is put into another non-enzyme centrifuge tube, and 500 μL of isopropanol is added. Bottom-up even mixing is performed, standing is performed for 10 min at a room temperature, after standing ends, centrifuging is performed for 10 min at 4° C. and 12000 r/min, supernate is discarded, RNA is left as white precipitates at the bottom of the centrifuge tube, 1 mL of a 75% ethanol solution prepared from DEPC water is added, vortex shaking resuspending is performed, centrifuging is performed for 5 min at 4° C. and 7500 r/min, supernate is discarded, and the RNA is naturally evaporated and dried at a room temperature. 30 μL of RNase free water is added to the dry RNA, after the RNA is dissolved, a concentration and purity of the RNA are measured through a Nanodrop, and a quality of the RNA is detected through agarose gel electrophoresis. With the total extracted RNA as a template, c DNA is synthesized through reverse transcription according to operating steps in a specification of a PrimeScript $1^{st}$ Strand cDNA Synthesis Kit from TaKaRa Company and is preserved at −20° C.

q RT-PCR reaction system and conditions:

PCR amplification is performed through a Bio-Rad® CFX96™ real-time fluorescence quantification PCR amplifier, and fluorescence signals are read.

q RT-PCR reaction system of virulence genes of *C. jejuni* is as follows:

| iTaq ™ Universal SYBR ® Green Supermix | 10 μL |
| Upstream primers (10 μmol/L) | 1 μL |
| Downstream primers (10 μmol/L) | 1 μL |
| cDNA template | 1 μL |
| ddH$_2$O | 7 μL | q RT-PCR reaction conditions of virulence genes of *C. jejuni* are as follows:

predegeneration for 30 s at 95° C., degeneration for 5 s at 95° C., and annealing for 30 s at 60° C. (40 cycles).

Figure 5:
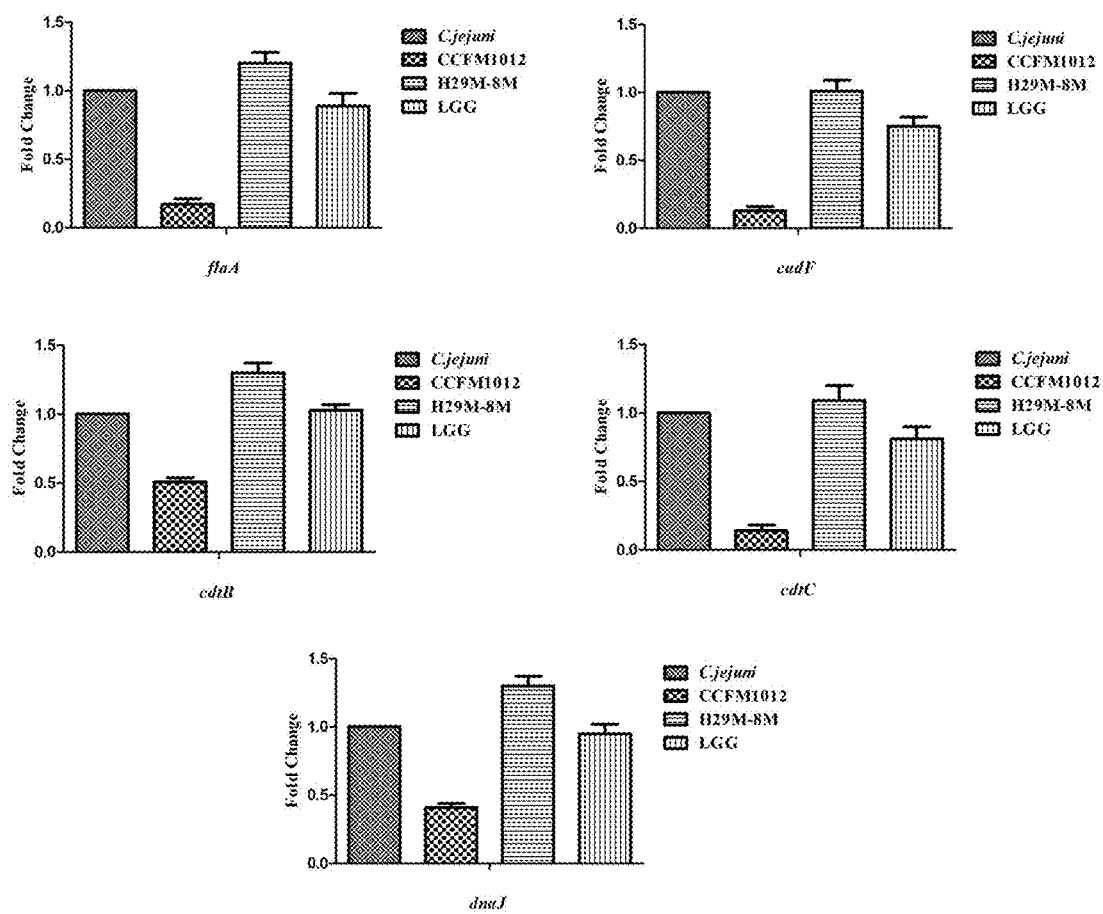
FIG. 5 is a schematic diagram that shows variations of transcriptional activity of virulence genes flaA, cadF, cdtB, cdtC and dnaJ of *C. jejuni* in intestines of mice of mice infected with *C. jejuni* after intervention by the strain of the disclosure.

Results are shown in FIG. 5, the *P. pentosaceus* CCFM1012 can effectively restrain transcriptional levels of virulence factors flaA, cadF, cdtB, cdtC and dnaJ of in-vivo *C. jejuni* of mice, and its corresponding virulence factor folds can be lowered to 0.17, 0.13, 0.51, 0.14 and 0.41, which shows that the *P. pentosaceus* CCFM can achieve an antagonism effect on infection of *C. jejuni* by lowering the levels of the virulence factors of the *C. jejuni*.

Example 7: Use of *P. pentosaceus* CCFM1012 of the Disclosure to Make Fermented Food Containing the Same Fresh vegetables are selected, cleaned and squeezed into juice, the juice is then instantaneously sterilized at a high temperature and instantly cooled to 37° C. after being hot sterilized for 2 s at a high temperature of 140° C., and then a bacterial leavening agent of the *P. pentosaceus* CCFM1012 prepared in the disclosure is then introduced, so that a concentration of the juice reaches $10^6$ CFU/mL or above, the juice is cryopreserved at a temperature of 4° C., and thus a fruit and vegetable beverage containing viable bacteria of the *P. pentosaceus* CCFM1012 of the disclosure is obtained.

By using the disclosure, other fermented food can be produced and prepared through fermentation of the *P. pentosaceus* CCFM1012. The fermented food includes solid food, liquid food and semi-solid food. The fermented food includes dairy products, bean products and fruit and vegetable products. The dairy products include milk, sour cream and cheese. The fruit and vegetable products include cucumber products, carrot products, beet products, celery products and cabbage products.

The fermented food can restrain the growth of *C. jejuni*, reduce an in-vivo colonization rate of the *C. jejuni*, lower the expression levels of virulence genes flaA, cadF, cdtB, cdtC and dnaJ of the *C. jejuni*, and relieve physiological damage caused by infection of the *C. jejuni*.

Example 8: Use of *P. pentosaceus* CCFM1012 of the Disclosure to Make Feed Additive Containing the Same The feed additive is a liquid or powder containing the *P. pentosaceus* CCFM1012, and its preparing process is as follows: the cryopreserved *P. pentosaceus* CCFM1012 is transferred into an MRS liquid culture medium twice (18 h each time) according to a ratio of 2% (v/v) and is then activated to obtain a second-stage seed solution, the second-stage seed solution is inoculated into a fermentation tank containing an MRS medium according to an inoculation quantity of 5% for fermentation culture and is then aerobically cultured for 48 h at 37° C., a fermentation broth is centrifuged at 8000 rpm to obtain bacterial sludge, water accounting for 90% of a mass of the bacterial sludge, saccharose accounting for 40% of the mass of the bacterial sludge, maltodextrin accounting for 50% of the mass of the bacterial sludge and whey powder accounting for 50% of the mass of the bacterial sludge are added, stand for 30 min at a room temperature and are then mixed with a solution which contains sodium carboxymethylcellulose accounting for 40% of the mass of the bacterial sludge, microcrystalline cellulose 8 times the mass of the bacterial sludge, sodium alginate 10 times the mass of the bacterial sludge, calcium chloride 10 times the mass of the bacterial sludge and water 20 times the mass of the bacterial sludge, and then wet granulating is performed and cyclone drying is performed at 37° C. to obtain the feed additive finished product containing the *P. pentosaceus* CCFM1012. The finished product has a viable count of $1\times10^{10}$ CFU/g or above. The *P. pentosaceus* CCFM1012 feed additive may be directly mixed into a finished feed product according to a mass ratio of a culture solution to a feed being 0.5-2% for feeding poultry and livestock, thereby reducing the infection and carrying of *C. jejuni* in poultry and livestock, and may also be evenly mixed with original feed materials and fermented for several days to prepare a feed. A preparation process is as follows: smashed wheat bran, bean pulp and rice bran are selected and evenly mixed according to a mass ratio of 8:1:1 with water to make a water content of the material reach 35-40% and a content of basic protein reach about 18%, the *P. pentosaceus* CCFM1012 feed additive is dissolved in advance, then inoculated into a solid material according to an inoculation quantity of 0.5% (mass ratio), and evenly mixed at a controlled temperature of about 37° C., and after anaerobic culture for 72 h, the fermented material is dried at a low temperature not higher than 45° C. and is then sealed and cryopreserved at 4° C. A viable count of the *P. pentosaceus* CCFM1012 in the feed additive is not lower than $5\times10^8$ CFU/g. The feed additive can reduce the infection and carrying of *C. jejuni* in poultry and livestock.

Example 8: Preparation of Medicine Containing *P. pentosaceus* CCFM1012

The *P. pentosaceus* CCFM1012 is transferred into an MRS liquid culture medium twice (18 h each time) according to a ratio of 2% (v/v) and is then activated to obtain a second-stage seed solution, the second-stage seed solution is inoculated into a fermentation tank containing an MRS medium according to an inoculation quantity of 5% for fermentation culture and is then aerobically cultured for 48 h at 37° C., a fermentation broth is centrifuged at 8000 rpm to obtain bacterial sludge, and the bacterial sludge is compatible with a pharmaceutically acceptable carrier to prepare a liquid preparation, a powder or a granule.

Although the disclosure has been disclosed as above in preferred examples, it is not intended to limit the disclosure. Various modifications and variations can be made by those of skilled in the art without departing from the spirit and scope of the disclosure, and thus the protection scope of the disclosure should be defined by claims.

What is claimed is:

1. A composition comprising *Pediococcus pentosaceus* (*P. pentosaceus*) CCFM1012, deposited on Feb. 11, 2018, at the Guangdong Microbial Culture Collection Center, Guangdong Institute of Microbiology, Guangzhou, China, under GDMCC No. 60331, wherein:
   (a) the composition is a fermented food prepared by fermenting the *P. pentosaceus* CCFM1012; the fermented food comprises dairy products, bean products and fruit and vegetable products; the dairy products comprise milk, sour cream and cheese; and the fruit and vegetable products comprise cucumber, carrot, beet, celery and cabbage products,
   (b) the composition is a microbial preparation, or
   (c) the composition is a feed additive.

2. The composition according to claim 1, wherein the microbial preparation is a cell culture fluid of the *P. pentosaceus* CCFM1012.

3. The composition according to claim 2, wherein the cell culture fluid is a cell culture fluid obtained by culturing the *P. pentosaceus* CCFM1012 in an MRS medium.

4. The composition according to claim 1, wherein the *P. pentosaceus* CCFM1012 has a cell concentration of larger than or equal to $1 \times 10^7$ CFU/mL.

5. The composition according to claim 1, wherein the microbial preparation is a freeze-dried preparation comprising viable cells of the *P. pentosaceus* CCFM1012, and is prepared by fermenting the *P. pentosaceus* CCFM1012 in an MRS medium, collecting bacterial cells, mixing the bacterial cells with a cytoprotective agent and then performing a freeze-drying treatment.

6. The composition according to claim 1, wherein the feed additive is a feed additive finished product containing the *P. pentosaceus* CCFM1012 with a viable count of larger than or equal to $1 \times 10^{10}$ CFU/g, and is obtained by mixing bacterial cells of the *P. pentosaceus* CCFM101 with sodium carboxymethylcellulose, microcrystalline cellulose, sodium alginate, calcium chloride and water and performing wet granulating and drying.

7. A method of preparing a *Campylobacter jejuni* infection antagonism medicine, comprising the composition of claim 1.

8. The method according to claim 7, further comprising:
   restraining growth of *C. jejuni*;
   reducing an in-vivo colonization quantity of the *C. jejuni*;
   lowering expression levels of virulence genes flaA, cadF, cdtB, cdtC and dnaJ of the *C. jejuni*; and
   relieving physiological damage caused by infection of the *C. jejuni*.

9. The method according to claim 8, wherein the medicine is a liquid, a powder, or a granule comprising the *P. pentosaceus* CCFM1012.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
agactctcct gttcgtatgt at                                                  22

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
atgataatat cttcgccaag tt                                                  22

<210> SEQ ID NO 3
<211> LENGTH: 19
<212> TYPE: DNA
<213> ORGANISM: Artificial Sequence
<220> FEATURE:
<223> OTHER INFORMATION: Synthetic DNA

<400> SEQUENCE: 3
gctatggctg tgatggata                                                      19

<210> SEQ ID NO 4
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
tgagttacgg tgatgttgt                                                      19

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
actattcttg aaggacatac a                                                   21
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
cgaggattat cttgaccata                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
attgatgaat atgagtggaa t                                             21

<210> SEQ ID NO 8
<211> LENGTH: 18
<212> TYPE: DNA
<213> ORGANISM: Artificial Sequence
<220> FEATURE:
<223> OTHER INFORMATION: Synthetic DNA

<400> SEQUENCE: 8
tgtagtaggt ggaggtaa                                                 18

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
tcagctgtgc aaattcgttc                                               20

<210> SEQ ID NO 10
<211> LENGTH: 22
<212> TYPE: DNA
<213> ORGANISM: Artificial Sequence
<220> FEATURE:
<223> OTHER INFORMATION: Synthetic DNA

<400> SEQUENCE: 10
aaataggatc tagggtgcaa gg                                            22

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
agtgtcgagc ttaatatccc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA
```

```
<400> SEQUENCE: 12
ggcgatgatc ttaacataca                                              20
```